United States Patent
Struhl (10) Patent No.: US 8,162,997 B2
(45) Date of Patent: Apr. 24, 2012

(54) DEVICE FOR TREATMENT OF ACROMIOCLAVICULAR JOINT DISLOCATIONS

(76) Inventor: Steven Struhl, Harrison, NY (US)

( * ) Notice: Subject to any disclaimer, the term of this patent is extended or adjusted under 35 U.S.C. 154(b) by 677 days.

(21) Appl. No.: 12/290,939

(22) Filed: Nov. 5, 2008

(65) Prior Publication Data
US 2009/0182335 A1 Jul. 16, 2009

Related U.S. Application Data

(60) Provisional application No. 61/001,818, filed on Nov. 5, 2007.

(51) Int. Cl.
*A61B 17/04* (2006.01)
(52) U.S. Cl. ............. 606/300; 606/232; 623/13.11; 623/13.14
(58) Field of Classification Search ............. 606/74, 606/232, 300; 623/13.11, 13.14
See application file for complete search history.

(56) References Cited

U.S. PATENT DOCUMENTS

| | | | |
|---|---|---|---|
| 4,754,749 A * | 7/1988 | Tsou .................. | 606/304 |
| 5,041,129 A | 8/1991 | Hayhurst et al. | |
| 5,645,588 A | 7/1997 | Graf et al. | |
| 6,117,160 A * | 9/2000 | Bonutti ............... | 606/215 |
| 6,517,578 B2 * | 2/2003 | Hein ................... | 623/13.13 |
| 6,533,802 B2 | 3/2003 | Bojarski et al. | |
| 7,530,990 B2 * | 5/2009 | Perriello et al. ...... | 606/232 |
| 7,875,057 B2 * | 1/2011 | Cook et al. .......... | 606/232 |
| 7,901,431 B2 * | 3/2011 | Shurnas ............... | 606/232 |
| 2003/0130694 A1 * | 7/2003 | Bojarski et al. ..... | 606/228 |
| 2004/0133238 A1 * | 7/2004 | Cerier ................. | 606/232 |
| 2007/0016208 A1 * | 1/2007 | Thornes .............. | 606/72 |
| 2007/0270804 A1 * | 11/2007 | Chudik ................ | 606/60 |

OTHER PUBLICATIONS

S. Kim, et al., Arthroscopic Knot Tying, Techniques in Shoulder & Elbow Surgery, vol. 4, No. 2 (2003) at pp. 35-43.
Lippincott, et al., Your sutures are loose, but new devices are coming to the rescue, www.laparoscopy.com/update/jul00.html (Jul. 2000).

\* cited by examiner

*Primary Examiner* — Thomas C. Barrett
*Assistant Examiner* — Michael T Schaper
(74) *Attorney, Agent, or Firm* — Leo Zucker (57) ABSTRACT

A surgical fastener system for acromioclavicular (AC) joint dislocations, includes a first fastener having an elongate body, and an inner pair of openings centered on the long axis of the body. A closed loop stitch passes through the openings, and the length of the stitch corresponds to the depth of a passage defined between the top of a first hole bored through a patient's clavicle, and the bottom of a second hole bored through the coracoid in axial alignment with the first hole. A second fastener has an elongate body arranged to slide under a portion of the loop stitch that protrudes from the top of the hole in the clavicle, after the first fastener is set beneath the coracoid and the stitch is pulled upward through the passage. In an alternate embodiment, the second fastener also has an inner pair of openings for passing and engaging the loop stitch.

3 Claims, 9 Drawing Sheets

DEVICE FOR TREATMENT OF ACROMIOCLAVICULAR JOINT DISLOCATIONS

CROSS REFERENCE TO RELATED APPLICATION

This application claims priority under 35 U.S.C. §119(e) of U.S. Provisional Patent Application No. 61/001,818 filed Nov. 5, 2007, entitled "Double Endobutton Technique for Repair of Complete Acromioclavicular Joint Dislocations", which is incorporated by reference.

BACKGROUND OF THE INVENTION

1. Field of the Invention

The present invention concerns surgical devices for repairing bone fractures or dislocations.

2. Discussion of the Known Art

Traumatic separation of the acromioclavicular (AC) joint is common, particularly among athletes. Complete rupture of the coracoclavicular ligament is common in the more severe grades of injury (type 3 or greater). Although surgical techniques for repairing or reconstructing the ligament have evolved over the last several decades, a gold standard has not yet emerged.

The proper course of initial treatment of an acute type 3 separation of the AC joint remains controversial. Although studies have demonstrated successful outcomes with nonoperative treatment, others have noted poor outcomes in over 40% of patients. Many of these patients have subsequent surgical treatment for ongoing symptoms of both pain and/or weakness. Long-term follow-up has shown residual symptoms in most patients treated nonoperatively. This has led to a commonly accepted recommendation of surgical treatment in high-level athletes or high-demand manual laborers. But even among patients with lower demand levels, a recent study has shown a poor outcome in 20% of non-athletes, and an additional 15% of patients reported significant symptoms of weakness.

The weight of the arm places a constant deforming force on a surgical fixation construct during biologic healing. In the acute setting, there is a robust healing response after ligament rupture, and additional grafting may not be necessary as long as the initial fixation can remain stable during the healing process. In the chronic setting, it is necessary to add biologic graft material to the fixation construct to ensure long-term stability and function. During the healing process, graft material is likely to weaken and stretch during the course of revascularization. Thus, when a fixation device is used in conjunction with a graft, it is at risk for implant failure if the graft deforms and stretches.

Surgical treatment has shown higher success rates in recent studies, but many of the techniques have become associated with significant implant related complications. Failure to establish a treatment with a reproducible outcome and a consistently low complication rate has therefore led most sports medicine specialists to continue to recommend non-operative management for the initial treatment of type 3 AC joint separations. For example, in a recent survey of over 500 members of the American Orthopaedic Society for Sports Medicine, more than 80% of respondents preferred non-operative treatment for initial management.

Prior techniques using various forms of hardware fixation, such as the Bosworth screw, have fallen out of favor because of hardware failures and the need for a second procedure to remove the hardware. The Weaver-Dunn procedure, first described in 1972, avoids the use of metallic implants and continues to be popular notwithstanding an originally reported failure rate of 28% in a small series of 15 patients. Attempts to improve the original Weaver-Dunn technique have involved various methods of non-metallic fixation to stabilize the AC joint. Notwithstanding the success of these methods, implant-related problems including infection, soft tissue reactivity, and fractures have been identified. These implant-related problems have led to development of purely biologic constructs that use allograft or autograft to reconstruct the coracoclavicular complex.

Biomechanical studies have yielded techniques for re-creating the native anatomy more accurately, and finding materials that can tolerate cyclic loading without deformation or failure. The ultimate strength, stiffness, and load elongation curves of the native complex have been measured against various repair constructs, and testing has been performed with both simple load to failure modes as well as response to cyclical loading to simulate postoperative conditions. Traditional procedures like Weaver-Dunn have been shown to be much weaker and more compliant than the native ligament, thereby explaining the frequently observed high failure rate of that procedure. A common modification involves stabilizing the joint by placing a cerclage material around the base of the coracoid and through a hole in the clavicle. Thick, robust materials such as polidioxanone bands or large tendon grafts have shown comparable strength relative to the native complex; however, their load-elongation curves indicate lower stiffness in most of the tested materials. Significantly, cerclage techniques have also been found to be non-anatomical as the fixation method drags the distal clavicle anteriorly. One study showed that even when the drill hole is placed within 2 mm of the anterior edge of the clavicle, the clavicle is pulled anteriorly. This malreduction is likely to lead to abnormal forces placed on the construct, weakening the construct with time as cyclical forces act on it constantly during the healing process.

Fixation placed in anatomically correct positions should improve implant stability and response to cyclical loads. Techniques have been described that achieve stability by placing grafts or fixation devices through anatomically placed boles in the clavicle and coracoid. An ideal procedure would use a fixation construct that not only restores the normal biomechanics of the ligament complex, but also maintains reduction throughout the biologic healing process.

U.S. Pat. No. 5,645,588 (Jul. 8, 1997), incorporated by reference, shows a graft attachment device for use arthroscopically to reconstruct the anterior cruciate ligament (ACL) in the knee. The device has a rectangular, bar-shaped body of stainless steel or equivalent biocompatible material, 4 mm in width and 12 mm in length. A first pair of 0.062 inch diameter openings are formed near the opposite long ends of the device body, and a second pair of 0.78 inch diameter openings are formed along the long direction of the device body between the first pair of openings. A patellar tendon graft is linked to the device by two sutures both of which pass through the second pair of openings in the device, and the free ends of each suture are tied so that sutures form closed loops. Each one of a second pair of sutures passes through a corresponding one of the first pair of openings, and the free ends of the second pair are threaded through a slot at the end of a pin instrument that has been inserted though passages formed in the femur and the tibia. The device, together with the graft which is linked to the device, are pulled through the passages by the pin instrument until the device emerges from a passage at the upper femoral cortex. The device is then rotated and seated against the femoral cortex. See also U.S. Pat. No.

6,533,802 (Mar. 18, 2003), and U.S. Pat. No. 5,041,129 (Aug. 20, 1991), both of which are incorporated by reference.

SUMMARY OF THE INVENTION

According to the invention, a surgical fastener system for treatment of acromioclavicular (AC) joint dislocations, includes a first fastener including an elongate body having an outer pair of openings formed in the vicinity of opposite ends of the body, and an inner pair of openings formed between the outer pair. A portion of a closed loop stitch passes through the inner pair of openings, and the loop stitch has a length that corresponds to a measured depth of a passage defined between a top opening of a first hole bored through a patient's clavicle, and a bottom opening of a second hole bored through the coracoid in axial alignment with the first hole. A second fastener includes an elongate body having at least an outer pair of openings formed in the vicinity of opposite ends of the body. The body of the second fastener is dimensioned and arranged to be slid through a portion of the closed loop stitch that protrudes from the top opening of the first hole in the clavicle, after the first fastener is set beneath the coracoid and the loop stitch is pulled upward through the passage between the top opening of the first hole and the bottom opening of the second hole.

According to another aspect of the invention, the body of the second fastener also has an inner pair of openings for passing and engaging the loop stitch.

For a better understanding of the invention, reference is made to the following description taken in conjunction with the accompanying drawing and the appended claims.

DETAILED DESCRIPTION OF THE INVENTION

Figure 1:
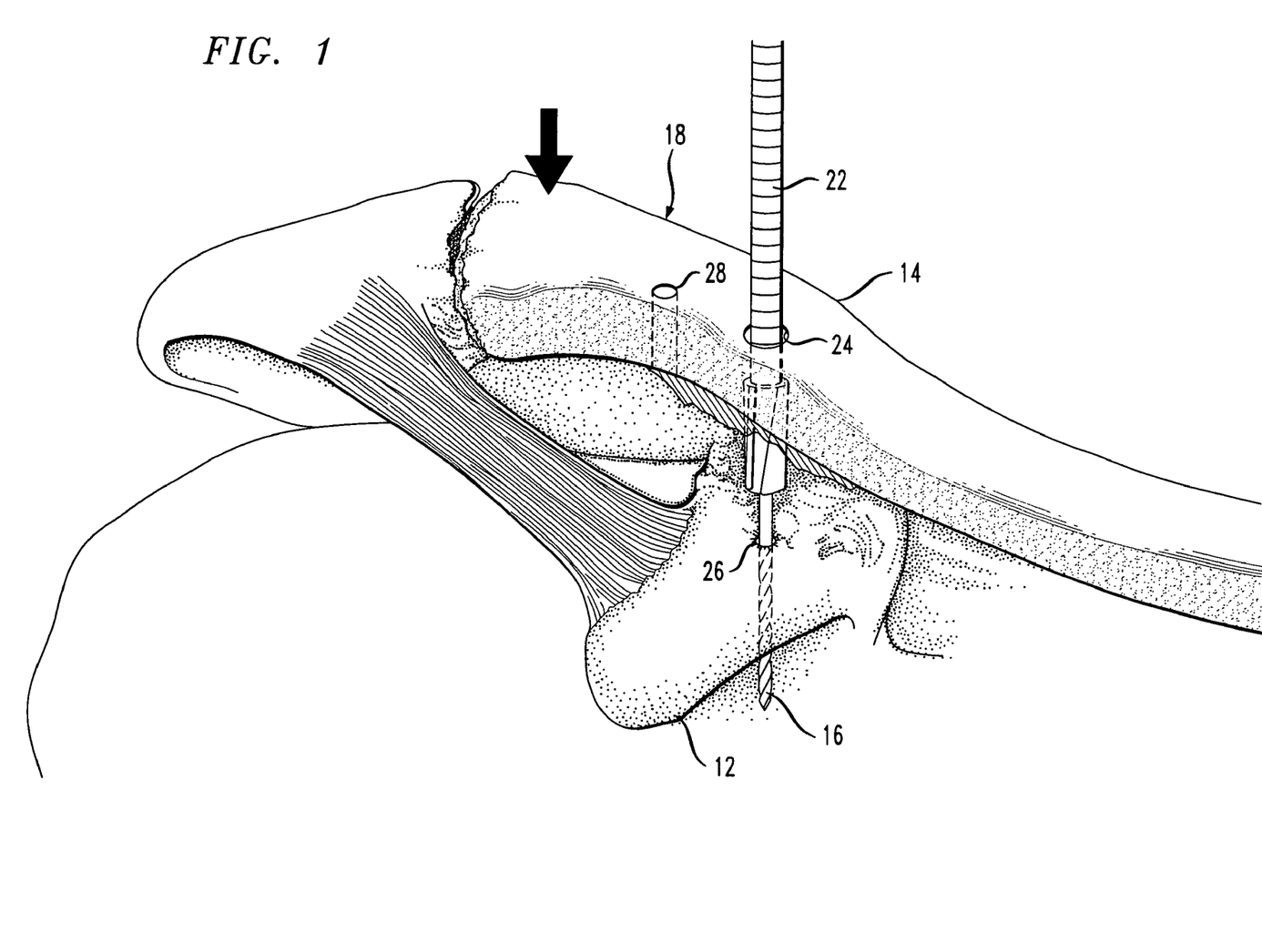
FIG. 1 shows an acromioclavicular joint being prepared for treatment with the inventive fastener system.

FIGS. 1 to 6 illustrate a surgical procedure for treatment of an AC joint dislocation, using a first embodiment of a fastener system according to the invention. In FIG. 1, a 2-inch incision is made from the palpable base of the tip of the coracoid 12, to the anterior edge of the distal clavicle 14. Medial and lateral skin flaps are developed. The deltoid is split in line with its fibers, and the coracoid 12 is identified and cleared off all the way to the base. The medial and the lateral edges of the coracoid 12 at the base are clearly identified.

The clavicle 14 is manually reduced, and while the reduction is being held, a drill tip guide wire 16 is drilled into the top of the clavicle 14 approximately 3 cm medial to the AC joint 18, and midway between the anterior and the posterior border of the clavicle. The drill hole should be directly over the base of the coracoid 12, and the drill wire 16 should be aimed slightly anteriorly. After drilling through the clavicle 14, the wire 16 should be easily visualized in between the clavicle and the coracoid 16. Once the tip of the wire 16 is confirmed to be entering the coracoid 12 well centered between the medial and the lateral edges, it is then drilled all the way through and out of the base.

A 4.5 mm dia. drill 22 is guided over the drill guide wire 16 to bore a first hole 24 through the clavicle 14, and another hole 26 (see FIG. 3) through the coracoid 12 in alignment with the clavicle hole 24. With the clavicle 14 well reduced, a depth gauge (not shown) is used to measure the length of a passage from the top opening of the bore hole 24 in the clavicle, to the bottom opening of the bore hole 26 in the coracoid. A 2.5 millimeter dia. drill hole 28 is bored in the clavicle 14, one cm lateral to the top of hole 24.

Figure 2:
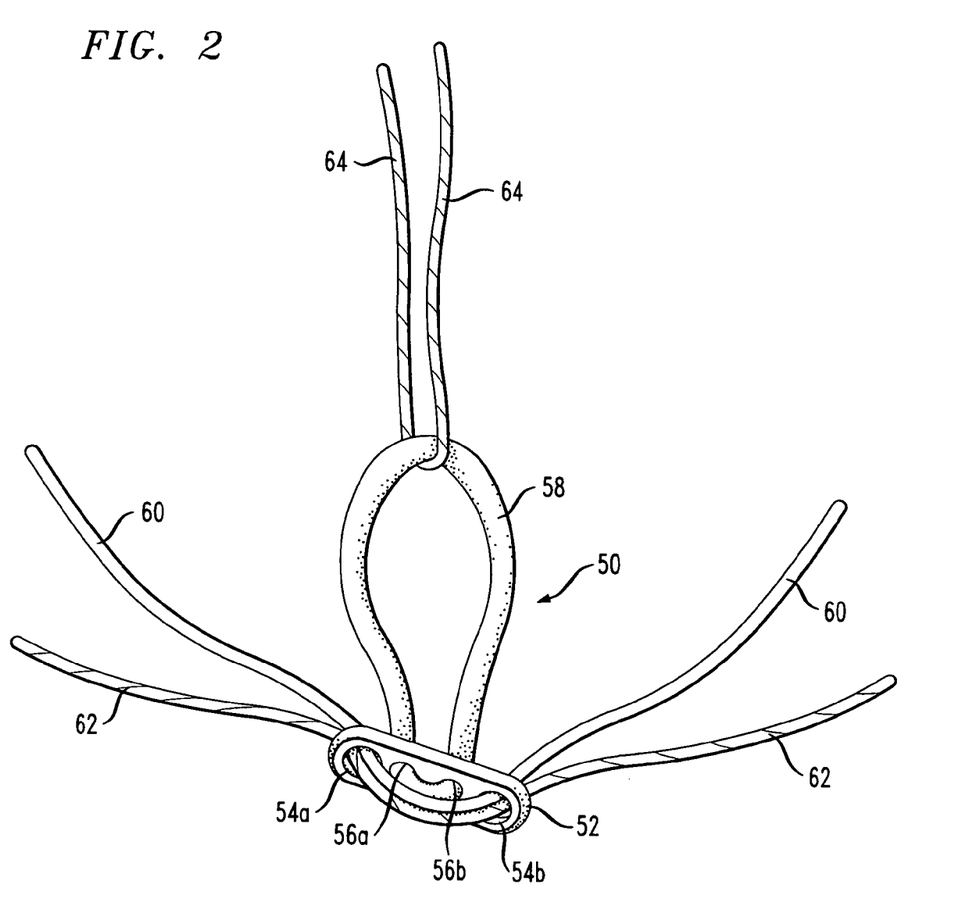
FIG. 2 shows a first fastener arranged with a lop stitch according to one embodiment of the inventive system.

A fastener 50 arranged according to the invention is shown in FIG. 2. The fastener 50 includes a sturdy elongate body 52 formed of surgical steel or an equivalent medically safe material. The fastener body 52 may measure, e.g., approx. 4 mm wide by 12 mm long. An outer pair of openings 54a, 54b are formed near the opposite short side ends of the fastener body 52, and an inner pair of openings 56a, 56b are centered on the long axis of the body 52 between the outer pair of openings 54a, 54b. An endless or closed loop stitch 58 engages the fastener 50 by passing through inner openings 56a, 56b in the fastener body 52. The stitch 58 may be formed, for example, by tying the ends of a suture strand together to form a loop whose length corresponds to that measured by the depth gauge noted above. The fastener body 52 with the closed loop stitch 58 may also be obtained from Smith & Nephew, Inc., of Memphis, Tenn. under the mark EndoButton®, or from ConMed of Largo, Fla. under the mark "XO Button".

As seen in FIG. 2, two number 5 Ethibond (or similar) sutures 60, 62 are placed through the outer pair of openings 54a, 54b in the body 52 of the fastener 50. A third suture 64 is passed through the apex of the loop suture 58 of the fastener 50. The suture 64 is preferably well marked so it can be used to identify the loop suture 58 through which it passes.

Figure 3:
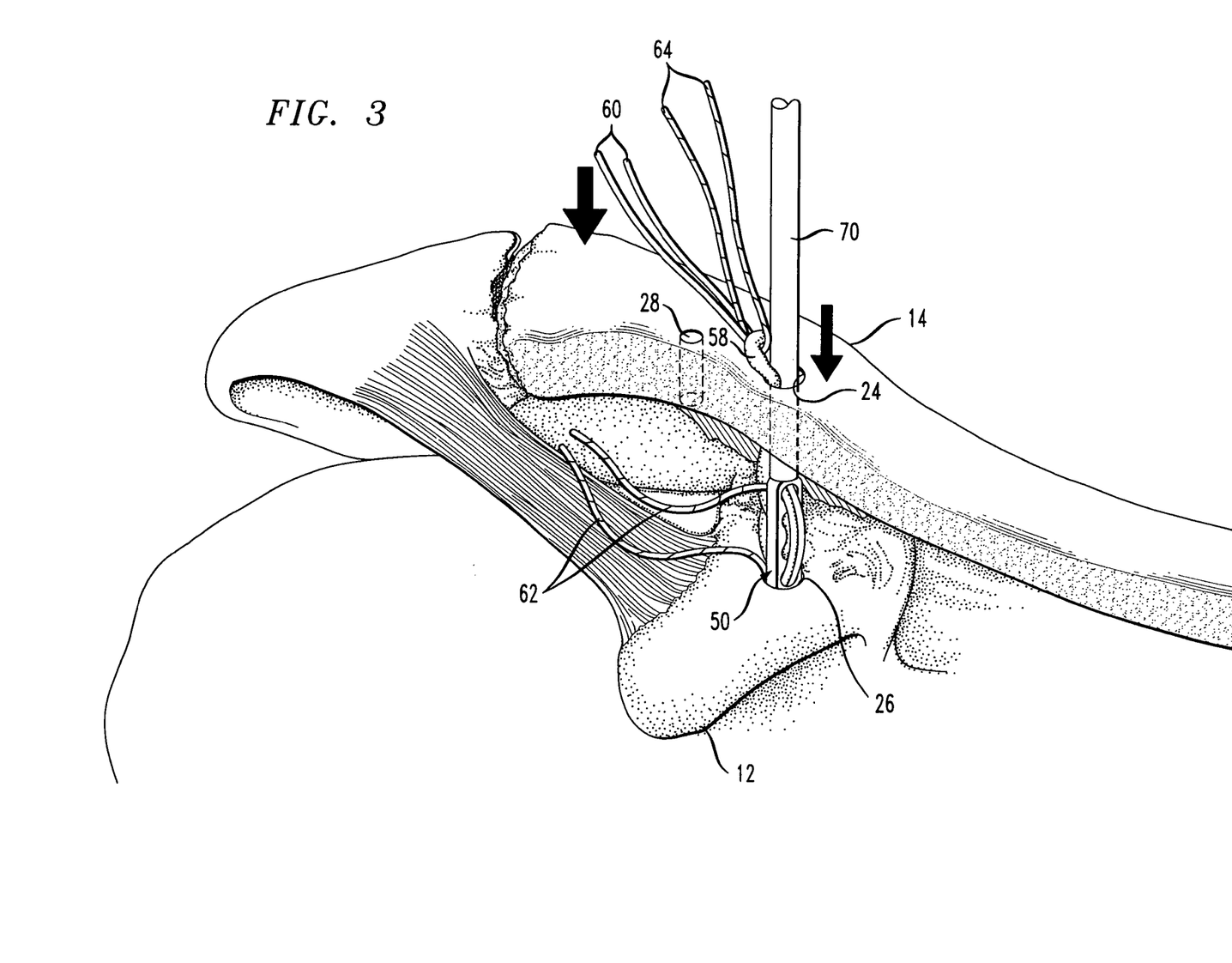
FIG. 3 shows the fastener in FIG. 2 inserted through holes that are bored in the clavicle and the coracoid in the joint in FIG. 1.
Figure 4:
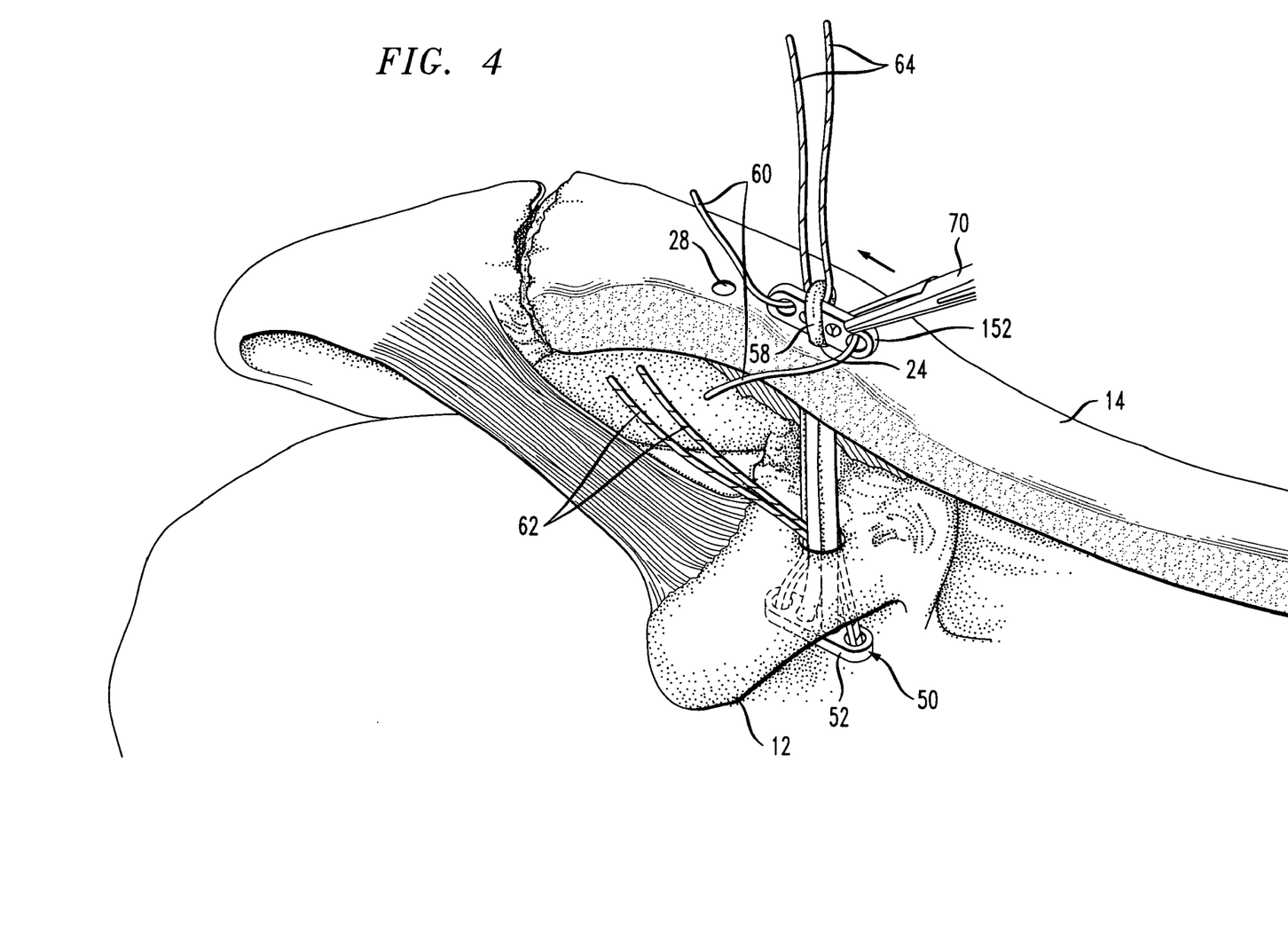
FIG. 4 shows the loop stitch pulled upward through the bored holes after the first fastener is set beneath the coracoid, and a second fastener is slid through a portion of the stitch that protrudes atop the clavicle.

The fastener 50 with its associated sutures 60, 62, 64 are vertically oriented and urged through the top of the clavicle 14 through the hole 24, using a 3.2-mm smooth cylindrical plunger 70. The fastener 50 is visualized in the space between clavicle 14 and coracoid 12, and it is pushed further to enter the coracoid hole 26 until the fastener "pops" out from the underside of the coracoid 12 as seen in FIG. 4. Then, by pulling the loop stitch 58 upward via the suture 64, the fastener 50 assumes the horizontal position in FIG. 4 to lock onto the underside of the coracoid 12. A pair of tails of one of the remaining sutures, e.g., suture 62, are pulled out of the interval between the coracoid 12 and the clavicle 14. This leaves the tails of one suture, e.g., suture 60 that is looped to the fastener body 52, available to exit from the top of the hole 24 in the clavicle 14 as shown in FIG. 3. With firm downward pressure on the clavicle 14 to maintain maximum reduction, the loop stitch 58 is pulled up through the hole 24. With a very firm upward pull on the loop stitch 58, the upper tip of the loop stitch will then protrude from the top of the clavicular hole 24.

In FIG. 4, a second button fastener body 152 which may be similar or identical in form to the fastener body 52 in FIG. 2, is held with a suture holder 70 and slid horizontally through the protruding loop of the stitch 58 until the body 152 is centered under the loop. It is preferred that the fastener body 152 be held with its long edge facing the clavicle 14, rather than lie flat against the bone. The suture tails 60 exiting the hole 24 at the top of the clavicle, are passed through a pair of openings formed near the opposite ends of the body 152. If the body 152 is formed with inner and outer pairs of openings like the fastener body 52, it is preferred to pass the suture tails 60 through the outer pair of openings as shown in FIG. 4.

Figure 5:
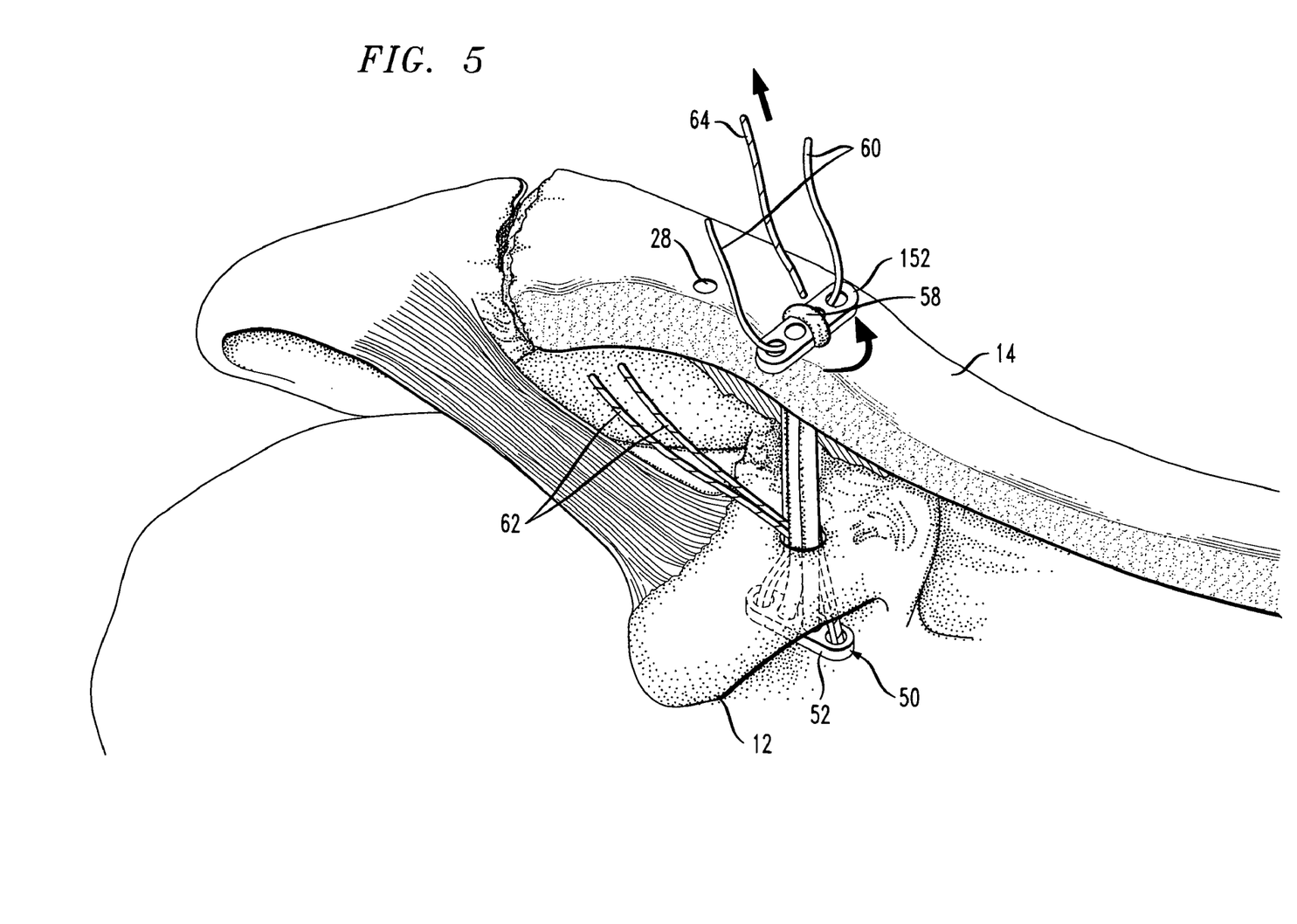
FIG. 5 shows the second fastener set in place atop the clavicle.
Figure 6:
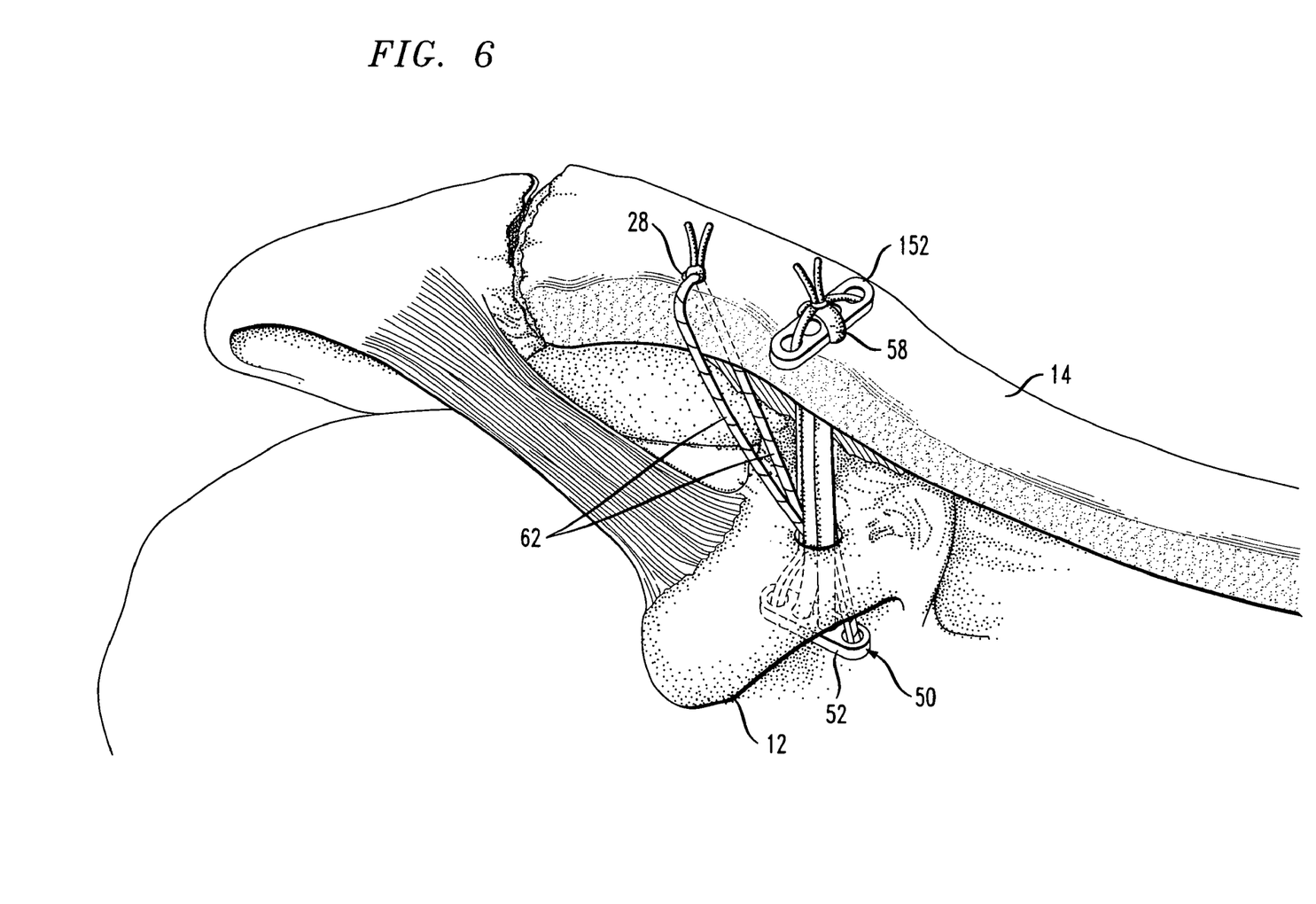
FIG. 6 shows the loop stitch locked in place about the body of the second fastener, and a suture tied to the clavicle through another hole bored in the clavicle.

The button fastener body 152 is turned with the suture holder 70 so it lies flat on the clavicle 14, so that the suture tails 60 exit upward from the openings in the body 152 as shown in FIG. 5. Suture 64 is withdrawn, and the suture tails 60 are tied across the top of the loop stitch 58 as shown in FIG. 6. This locks the stitch 58 in place and completes the reconstruction of the conoid portion of the coracoclavicular ligament. The suture tails 62 that were brought out of the coracoclavicular space are retrieved. One of the tails 62 is passed through the 2.5 mm drill hole 28 from beneath the clavicle 14, and the ends of the suture tails are tied at or near the top of the hole 28. This recreates the trapezoid portion of the coracoclavicular ligament.

Figure 7:
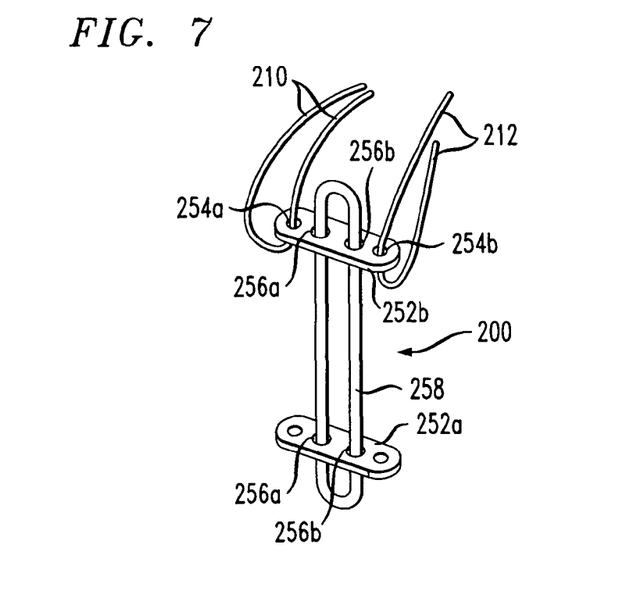
FIG. 7 shows another embodiment of the inventive fastener system, wherein the bodies of first and second fasteners are linked by a common closed loop stitch.

A fastener device 200 according to the invention is shown in FIG. 7. The device 200 includes two fastener bodies 252a, 252b each of which may be similar or identical in form to the fastener body 52 in FIG. 2. The fastener bodies 252a, 252b are linked by one endless or continuous loop 258 which passes through pairs of openings 256a, 256b formed in each of the bodies. Like the fastener body 52 in the first embodiment, at least the body 252b at the top of FIG. 7 also has an outer pair of openings 254a, 254b formed near the opposite ends of the body.

Figure 8:
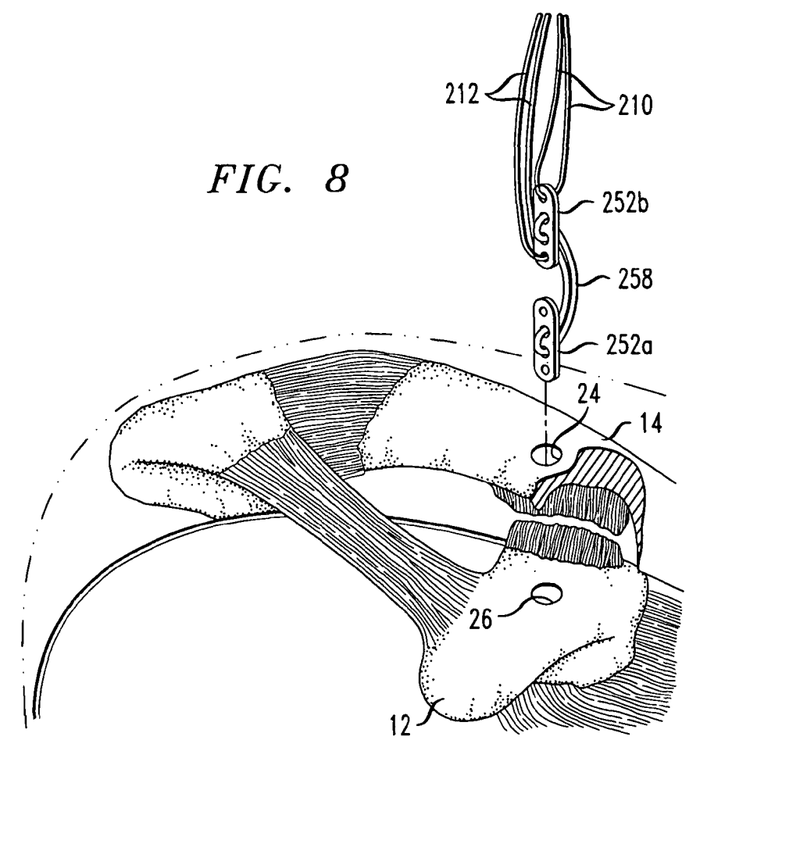
FIGS. 8 and 9 show the fasteners in FIG. 7 aligned for entry into and through the holes bored in the clavicle and the coracoid.
Figure 9:
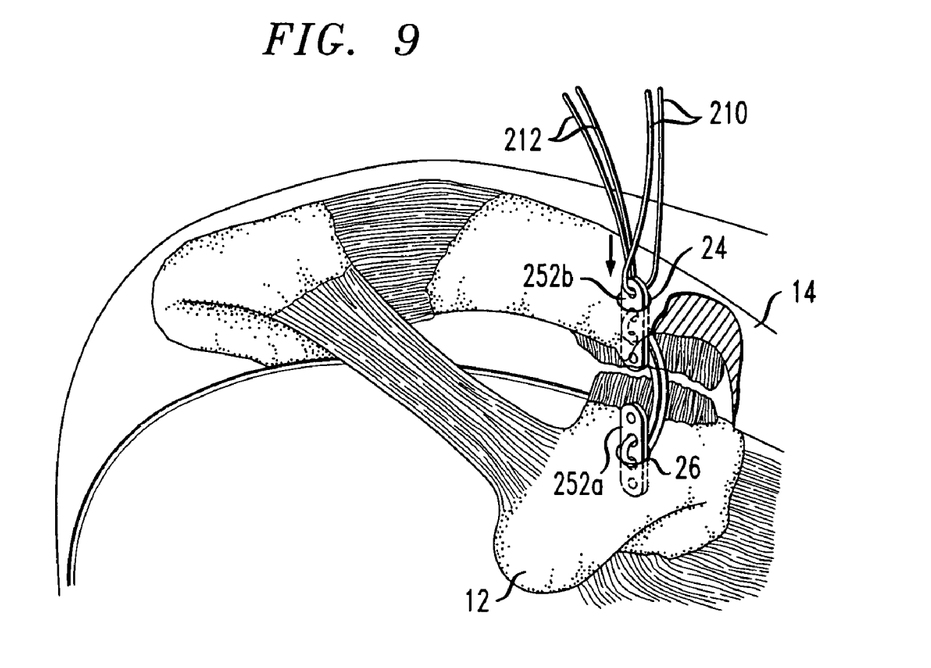
Figure 10:
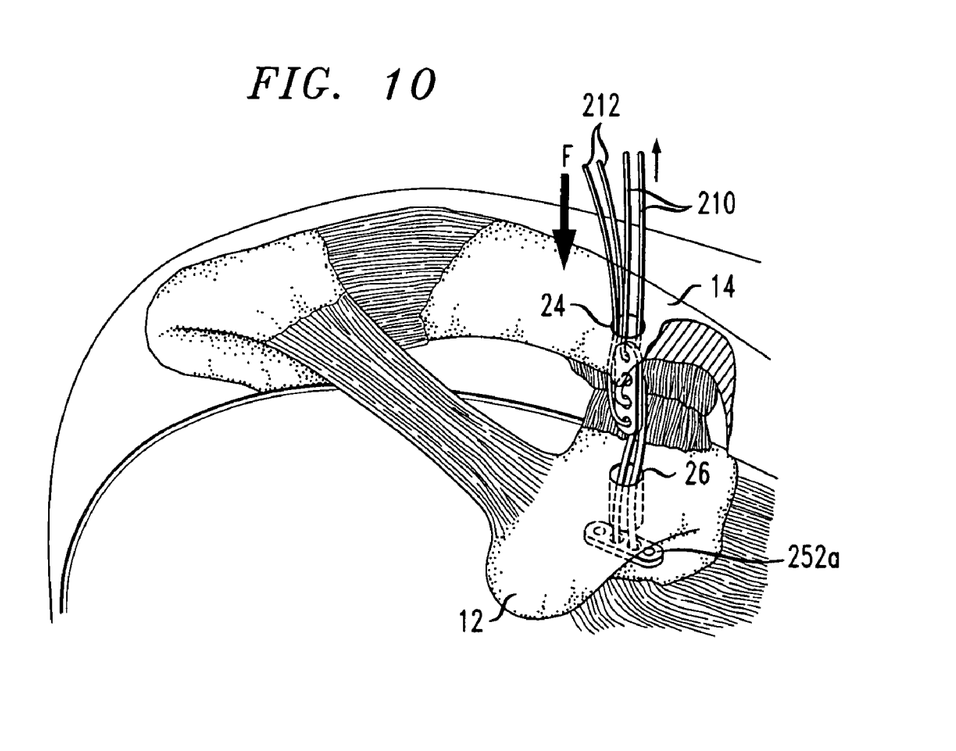
FIG. 10 shows a first one of the fasteners in FIG. 7 set beneath the coracoid.

Using the fastener device 200 of FIG. 7, the surgical procedure described above can be modified by threading two sutures 210, 212 through the outer openings 254a, 254b at opposite ends of the fastener body 252b at the top of FIG. 7. As depicted in FIGS. 8 and 9 the two fastener bodies 252a, 252b are oriented vertically in line with one another, and body 252a at the bottom of the loop 258 is fully inserted into the top of the hole 24 in the clavicle 14. Fastener body 252b is then inserted into the top of the hole 24 and urged downward with a plunger or other suitable tool so that the leading end of the body 252b advances the body 252a downward through the hole 24 to enter the top of the opening 26 at the top of the coracoid 12. The body 252a is then advanced further through the opening 26 until it fully exits the opening at the underside of the coracoid 12. Then, by pulling the sutures 210, 212 on the fastener body 252b upward, the fastener body 252a assumes a horizontal position in FIG. 10 to lock onto the underside of the coracoid 12.

Figure 11:
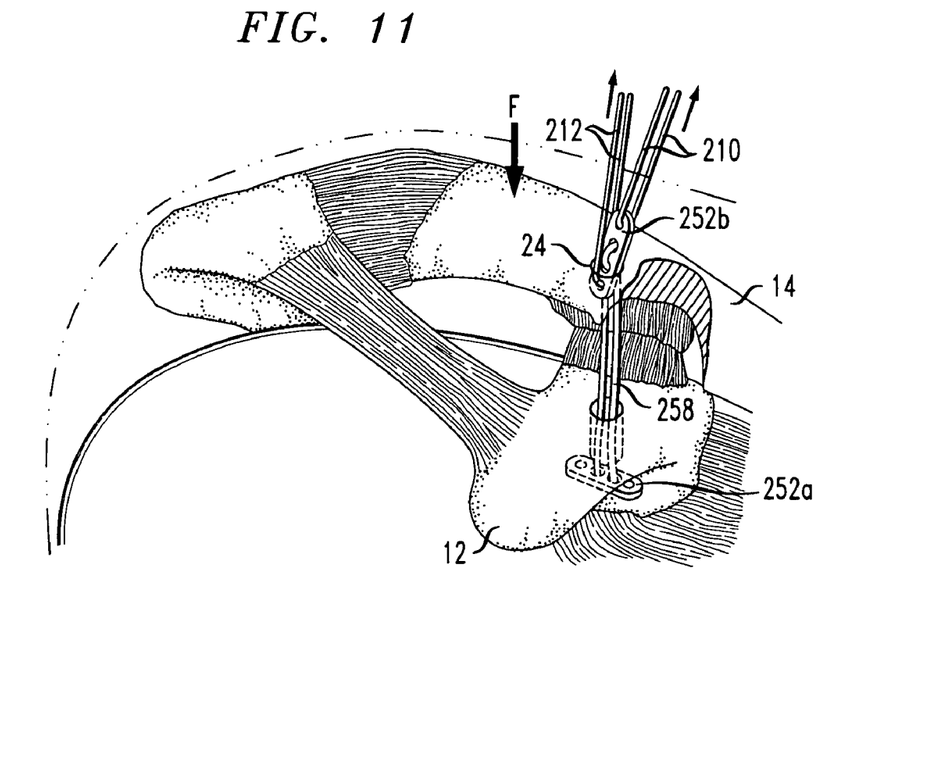
FIG. 11 shows the second fastener in FIG. 7 being withdrawn from the hole in the clavicle after the first fastener is set beneath the coracoid.
Figure 12:
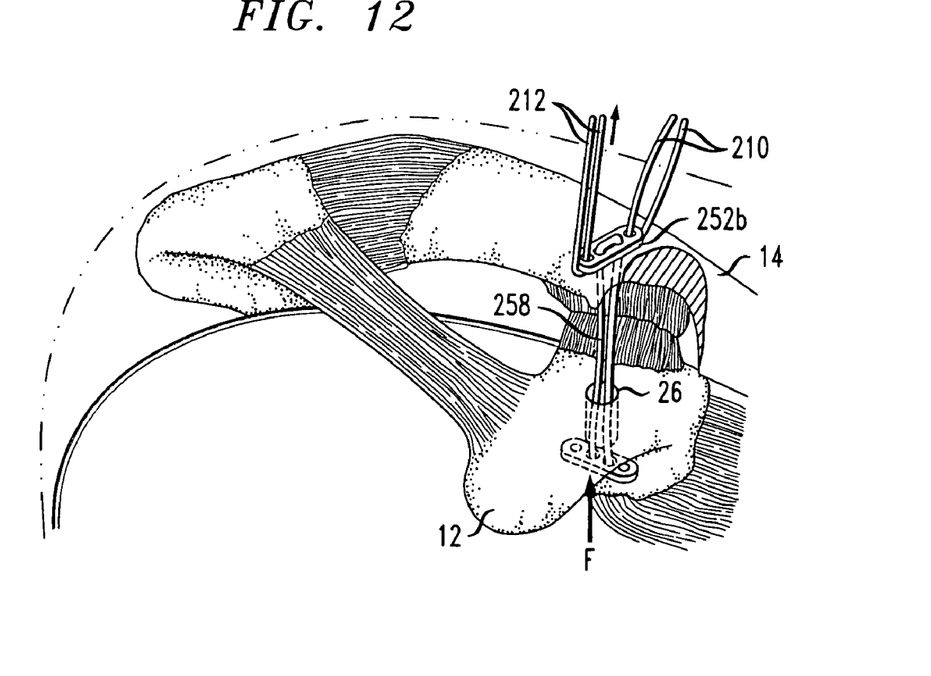
FIG. 12 shows the second fastener set in place atop the clavicle.

When the joint is fully reduced as depicted in FIG. 11 the sutures 210, 212 are pulled upward until the fastener body 252b exits the clavicular hole 24 as shown in the figure. Then by pulling upward on the suture 212 as represented in FIG. 12, the fastener body 252b is swivelled horizontally to lie flat on the surface of the clavicle 14 and thereby lock the joint reduction in place.

The fastener device 200 of FIG. 7 has an advantage over the fastener 50 of FIG. 2, by eliminating those steps in FIGS. 4, 5 and 6 wherein a second, free fastener body 152 is needed to be inserted through the top of the loop 58, and the suture 60 is tied so as to lock the fastener body 152 in place on the surface of the clavicle 14.

Fasteners as disclosed herein have been used successfully in cases of chronic type 3 or 4 AC separations. The fasteners are set in an anatomically correct fashion to reproduce the course of the conoid portion of the coracoclavicular ligament. The strength and stiffness of the fasteners have been proven to exceed the native ligament complex by approximately 40%. Deforming forces due to the weight of the arm are distributed along the surfaces of the fasteners rather than the suture material itself which passes through the openings in the fasteners, thereby minimizing the chance of a soft tissue reaction to the suture material. The sutures 62, which may be threaded through openings in the fastener bodies, can be used to recreate the course of the trapezoid component of the coracoclavicular ligament and add stability in the anteroposterior plane.

In addition, the required drill holes are relatively small (e.g., approx. 4 mm or less), allowing the implant to be used either as a stand-alone device or in conjunction with other biologic implants to improve long-term stability. Forming the suture material in a continuous loop eliminates problems of knot slippage associated with other types of suture fixation. The procedure is straightforward and requires only a small incision with minimal soft tissue dissection.

The inventive fasteners 50, 200 allow a knotless fixation to be obtained for repair and/or reconstruction of the shoulder coracoclavicular ligament, with reliable and predictable results. The fasteners are inserted through holes bored in the clavicle and the coracoid to reproduce the normal course of the conoid portion of the coracoclavicular ligament. The fasteners may be used alone or in conjunction with a variety of biologic materials depending on whether surgery is being performed in an acute or a chronic setting.

While the foregoing represents preferred embodiments of the invention, it will be understood by those skilled in the art that various modifications and changes may be made without departing from the spirit and scope of the invention, and that the invention includes all such modifications and changes as come within the bounds of the following claims.

I claim:

1. A surgical fastener system for treatment of a dislocation of a patient's acromioclavicular (AC) joint, comprising:
   a first fastener including an elongate first fastener body having an outer pair of openings formed in the vicinity of opposite ends of the body, and an inner pair of openings formed between the outer pair of openings;
   a second fastener including an elongate second fastener body having at least a first pair of openings;
   an endless loop stitch, a first portion of which passes through the inner pair of openings in the first fastener body and a second portion of which passes through the first pair of openings in the second fastener body, wherein the stitch is formed as a continuous closed loop and has a length that corresponds to a measured depth of a passage that extends between a top opening of a first hole bored through the patient's clavicle toward the coracoid at the dislocated AC joint, and a bottom opening of a second hole bored through the coracoid in axial alignment with the first hole, wherein the depth of the passage is measured when the dislocated joint is held in a reduced state:
   a first suture that passes through one opening of the outer pair of openings in the first fastener body, and a second suture that passes through the other opening of said outer pair of openings in the first fastener body; wherein, the second and the first fasteners are dimensioned and configured to be inserted in the stated order in the top opening in the clavicle, and to advance with the loop stitch and the first and the second sutures through the passage so that the second fastener exits the bottom opening in the coracoid and assumes a horizontal position to lock onto the underside of the coracoid;

the first and the second sutures are dimensioned and arranged for pulling the first fastener together with the first portion of the loop stitch upward through the passage after the second fastener is locked beneath the coracoid, and for swivelling the first fastener across the top opening in the clavicle to lock the dislocated joint in the reduced state thereby reproducing the normal course of the conoid portion of the coracoclavicular ligament; and including a third suture that passes through an opening in the second fastener body, and the third suture is dimensioned and arranged to extend through the second hole in the coracoid after the second fastener is locked beneath the coracoid, and to be tied at a third hole that is bored in the clavicle lateral to the top opening of the first hole in the clavicle thereby adding stability in the anteroposterior plane at the dislocated joint.

2. A surgical fastener system according to claim 1, wherein the second fastener body has a second pair of openings closer to opposite ends of the body than the first pair of openings in the body, and the third suture passes through the second pair of openings.

3. A surgical fastener system according to claim 1, wherein each of the first and the second fasteners measures approximately 4 mm wide by 12 mm long.

* * * * *